United States Patent [19]
Holbrook et al.

[11] Patent Number: 5,659,108
[45] Date of Patent: Aug. 19, 1997

[54] PROCESS FOR THE COMPLETE SATURATION OF HALOGENATED HYDROCARBON STREAMS CONTAINING UNSATURATED COMPOUNDS

[75] Inventors: Michael T. Holbrook; Lawrence A. Hebert; Katherine A. Pividal, all of Baton Rouge, La.; Celio Lume Pereira, Nachtigallenweg, Germany

[73] Assignee: The Dow Chemical Company, Midland, Mich.

[21] Appl. No.: 499,353

[22] Filed: Jul. 7, 1995

[51] Int. Cl.⁶ .............................. C07C 7/10; C10G 45/00
[52] U.S. Cl. .......................................... 585/833; 208/262.1
[58] Field of Search ...................... 208/262.1; 585/833

[56] References Cited

U.S. PATENT DOCUMENTS

| | | | |
|---|---|---|---|
| 4,895,995 | 1/1990 | James, Jr. et al. | 585/310 |
| 4,899,001 | 2/1990 | Kalnes et al. | 585/310 |

FOREIGN PATENT DOCUMENTS 0 541 871 A1   11/1991   European Pat. Off. ......... A62D 3/00

*Primary Examiner*—Glenn A. Caldarola
*Assistant Examiner*—In Suk Bullock

[57] ABSTRACT

A saturation process for essentially completely saturating unsaturated halogenated hydrocarbonaceous materials in a feedstock containing such unsaturated materials, employing a first recycle reactor for accomplishing the bulk of the saturation and a second, single pass, plug flow-type polishing reactor in combination.

18 Claims, 1 Drawing Sheet

PROCESS FOR THE COMPLETE SATURATION OF HALOGENATED HYDROCARBON STREAMS CONTAINING UNSATURATED COMPOUNDS

BACKGROUND OF THE INVENTION

The present invention is concerned in a broad sense with processes of the type described in several United States Patents assigned at issue to UOP, Inc., Des Plaines, Ill. USA wherein a saturated, halogenated (and especially chlorinated) organic feed is processed with a second halogenated organic feed containing significant amounts of unsaturated materials to produce hydrogen halide and an organic product stream having a reduced halogen content. Exemplary of the patents descriptive of these various processes are U.S. Pat. No. 4,899,001 to Kalnes et al., U.S. Pat. No. 4,895,995 to James, Jr. et al., and U.S. Pat. No. 4,929,781 to James, Jr. et al.

U.S. Pat. No. 4,818,368 to Kalnes et al., U.S. Pat. No. 4,882,037 to Kalnes et al., U.S. Pat. No. 4,923,590 to Kalnes et al., U.S. Pat. No. 4,927,520 to Kalnes et al. and U.S. Pat. No. 5,013,424 to James, Jr. et al. are related to the references mentioned in the preceding paragraph but are somewhat differently directed, in describing various processes and arrangements of unit operations for, e.g., "treating a temperature-sensitive hydrocarbonaceous stream containing a non-distillable component to produce a hydrogenated distillable hydrocarbonaceous product while minimizing thermal degradation of the hydrocarbonaceous stream", see col. 1, lines 14–19 of U.S. Pat. No. 4,818,368. A comparison of the contemplated "temperature-sensitive" hydrocarbonaceous streams of these references with the feedstocks, for example, of the U.S. Pat. No. 4,895,995 and U.S. Pat. No. 4,899,001 patents suggests that the arrangements described in these references can be employed for the same or essentially similar applications and uses, depending on whether a stream to be processed also contains non-volatile materials.

Copending, commonly-assigned U.S. patent application Ser. No. 08/499,695, filed concurrently herewith for "Integrated Process for Handling Saturated and Unsaturated Chlorinated Hydrocarbonaceous Waste and By-Products From Allyl Chloride and Propylene Oxide Processes", also describes processes for the simultaneous processing of saturated and unsaturated chlorinated hydrocarbonaceous materials, to produce an olefin product stream and hydrogen chloride in preferably anhydrous form. An exemplary use is for the processing of a finished 1,2-dichloropropane stream from a chlorohydrin process for manufacturing propylene oxide (as the saturated stream) and of one or more fractions from the fractionation of the products of an allyl chloride process, to produce hydrogen chloride and a propylene product stream for recycle to the allyl chloride process or chlorohydrin process for making propylene oxide.

A common feature of each of these various processes is the saturation of the unsaturated chlorinated/halogenated hydrocarbonaceous materials, under mild conditions designed to minimize the tendency of these materials to polymerize or form coke and to thereby cause deactivation of the catalyst in question under hydrogenation conditions. This mild saturation step is followed, directly or indirectly, by a hydrodechlorination step which is conducted under more severe conditions.

Because of the tendency of any unsaturated chlorinated hydrocarbonaceous materials remaining in the effluent from the mild saturation step to polymerize (coke) under the more severe conditions of the subsequent, hydrodechlorination step, however, there is a significant need to essentially completely saturate the unsaturated materials in the unsaturated chlorinated hydrocarbonaceous material-containing feedstock to the mild saturation segment of the process.

SUMMARY OF THE PRESENT INVENTION

The present invention meets this need in providing a novel and improved mild saturation process for essentially completely saturating unsaturated halogenated hydrocarbonaceous materials, and especially unsaturated chlorinated hydrocarbonaceous materials, in a feedstock containing such materials. Fundamentally, and unlike any of the aforementioned processes, the present invention accomplishes this end through a two-reactor arrangement wherein the first reactor includes a recycle loop and accomplishes the bulk of the saturation of the unsaturated materials in the feedstock, and the second reactor is a plug-flow, finishing reactor for accomplishing the remainder of the saturation.

The effect of this design, as opposed to a single reactor design employing a large recycle ratio, is to significantly reduce the size of the first reactor wherein the bulk of the saturation occurs and to thereby also reduce the amount and expense of the catalyst employed therein relative to a single reactor design. The second reactor is comparatively inexpensive, and the saturation catalyst employed therein should have a significantly reduced rate of deactivation as it will be exposed to lower olefin contents in the feed. Still other benefits and advantages will become apparent on further consideration.

DETAILED DESCRIPTION OF PREFERRED EMBODIMENTS

Figure 1:
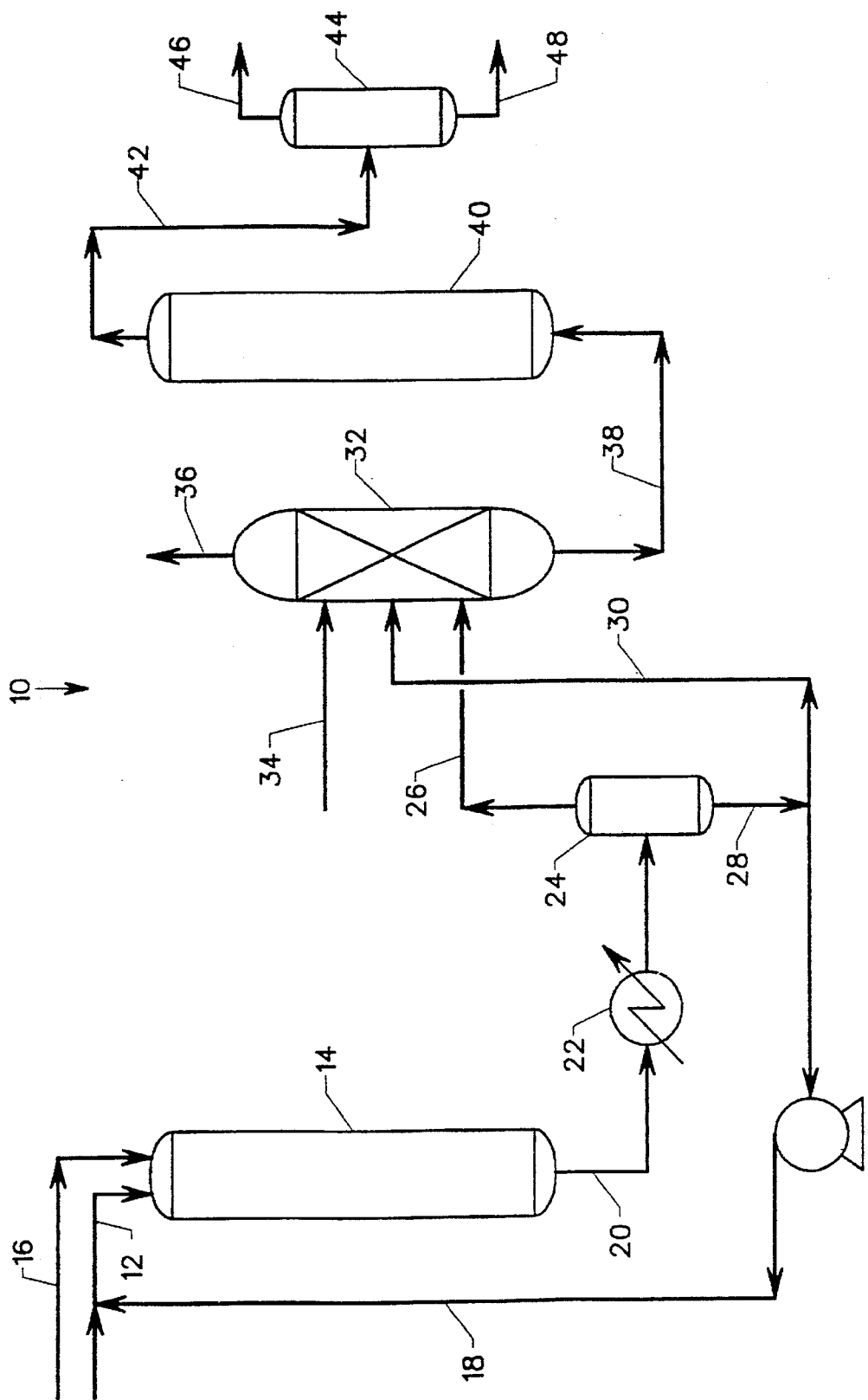
FIG. 1 is an illustration of a preferred process and apparatus of the present invention.

Turning now to FIG. 1, a process and apparatus of the present invention are illustrated in a preferred embodiment 10.

An incoming feed stream 12 to the apparatus 10 which contains significant amounts of unsaturated chlorinated hydrocarbonaceous materials, typically managed by dilution with an essentially saturated chlorinated hydrocarbonaceous stream and by the recycle of the more saturated recycle stream to contain no more than about 2 to 3 percent by weight of unsaturated materials in order to effectively manage the heat to be generated in the saturation of such unsaturated materials, is fed to a primary saturation reactor 14 along with a hydrogen stream 16.

A preferred application will find the feed stream 12 being comprised of dichloropropanes and dichloropropenes from an allyl chloride process as diluted with a finished 1,2-dichloropropane stream from a chlorohydrin-based propylene oxide process, optionally further comprising monochloropropenes from the fractionation overheads of the allyl chloride process. The feed stream 12 will also incorporate a liquid recycle portion 18 derived from the product stream 20 from the primary saturation reactor 14, which in the context of the preferred application and in the context particularly of a recycle process for recycling propylene to a chlorohydrin-based propylene oxide process and/or to an allyl chloride process (such as described in the aforementioned copending, commonly-assigned U.S. patent application Ser. No. 08/499, 695, filed concurrently herewith for "Integrated Process for Handling Saturated and Unsaturated Chlorinated Hydrocarbonaceous Waste and By-Products From Allyl Chloride and Propylene Oxide Processes"), will preferably contain any unsaturated materials in excess of about 1000 parts per million by weight in said product stream 20.

The primary saturation reactor 14 may suitably employ any conventional catalyst and any appropriate process conditions for saturating the unsaturated materials within feed stream 12 with preferably a minimum of polymerization and coking. Processes conducted primarily in the liquid phase or in the gas phase are suitably employed, but a liquid phase process is presently preferred.

U.S. Pat. No. 4,895,995 to James, Jr. et al. and U.S. Pat. No. 4,899,001 to Kalnes et al. are broadly descriptive and illustrative of catalytic saturation processes for saturating the types of materials found in the fractionation products of an allyl chloride process, and describe catalysts containing a metallic component having hydrogenation activity combined with a suitable refractory inorganic oxide carrier material of either synthetic or natural origin, preferred carrier materials being alumina, silica, carbon and mixtures of these. Metallic components identified as useful include those selected from Groups VIB and VIII of the Periodic Table, as set forth in the Periodic Table of the Elements, E. H. Sargent and Company, 1964, with the VIB metals of tungsten, molybdenum and chromium generally being present in an amount of from about 1 to about 20 weight percent, the iron-group metals in an amount of from about 0.2 to about 10 weight percent, and the noble metals of Grp. VIII in an amount of from about 0.1 to about 5 weight percent, all calculated on an elemental basis. Other metals contemplated include one or more of cesium, francium, lithium, potassium, rubidium, sodium, copper, gold, silver, cadmium, mercury and zinc.

Reaction conditions prescribed for these particular processes, as conducted with a fixed, ebulliated or fluidized catalyst bed, include a pressure of from atmospheric to about 2,000 psig, maximum catalyst bed temperatures of about 50 degrees Celsius to about 343 degrees Celsius, liquid hourly space velocities of from about 0.05 $hr^{-1}$ to about 20 $hr^{-1}$, and hydrogen circulation rates from about 200 standard cubic feet per barrel (SCFB) to about 100,000 SCFB. Preferred pressures are about 100 psig to about 1800 psig, with preferred hydrogen circulation rates being from about 300 SCFB to about 50,000 SCFB.

Based on initial indications at a pressure of 260 psig, reaction temperatures of from 10 degrees Celsius to about 100 degrees Celsius and preferably from about 30 degrees to about 60 degrees Celsius, a residence time of about 0.5 to about 1 hours and hydrogen to olefin molar feed ratios of about 1 to 1 to about 50 to 1 and preferably from about 2 to 1 to about 10 to 1, a preferred saturation catalyst would comprise palladium or platinum on a support selected to possess an appropriate pore size for a liquid phase saturation process.

The product stream 20 is at least partially condensed in exchanger 22, and passed into a high pressure vapor-liquid separator 24 to produce a vapor stream 26 containing excess hydrogen, lighter chlorinated hydrocarbons and propane and hydrogen chloride produced through hydrodechlorination in the primary saturation reactor 14, as well as a liquid stream 28 which is split into the liquid recycle portion 18 (in an amount corresponding to a recycle ratio which is preferably from about 6:1 to about 25:1, more preferably is from about 6:1 to about 15:1 and most preferably is from about 6:1 to about 12:1) and a liquid feed portion 30 to an absorber vessel 32.

Absorber vessel 32 preferably utilizes a chlorinated hydrocarbon solvent stream 34 for separating overhead in stream 36 substantially all of the hydrogen and other residual non-condensable gases in the vapor stream 26, in the manner of commonly-assigned, copending U.S. application Ser. No. 08/344,187, filed Nov. 23, 1994 for "Process for Extraction and Recovery of Anhydrous Hydrogen Chloride from Mixtures with Non-Condensable Gases", such application being incorporated herein by reference in pertinent part. The stream 36 is then useful for being recycled to the primary saturation reactor 14, or for being used in a subsequent hydrodechlorination reactor for hydrodechlorinating the saturated feed to this portion of an integrated process, in the manner of the above-referenced U.S. Pat. No. 4,899,001 to Kalnes et al., U.S. Pat. No. 4,895,995 to James Jr. et al. and U.S. Pat. No. 4,929,781 to James, Jr. et al. and commonly-assigned (with the present application) U.S. patent application Ser. No. 08/499/695 for an "Integrated Process for Handling Saturated and Unsaturated Chlorinated Hydrocarbonaceous Waste and By-Products From Allyl Chloride and Propylene Oxide Processes".

Absorber vessel 32 can also be equipped with a feboiler if necessary to remove residual non-condensables, and preferably is designed to effectuate as complete a separation as possible between the hydrogen and other non-condensables in vapor stream 26 and the hydrogen chloride and heavier, chlorinated hydrocarbonaceous materials in the vapor stream 26 and liquid feed portion 30 from the product stream 20.

As related in copending U.S. application Ser. No. 08/344, 187 the chlorinated hydrocarbon solvent stream 34 fed to the top of the packed absorber vessel 32 can in principle be any mono-, di- or trichlorinated hydrocarbon or can be a mixture of these, but conveniently and preferably is finished 1,2-dichloropropane or a like, saturated chlorinated hydrocarbon to be hydrodechlorinated in the subsequent hydrodechlorination portion of an integrated recycle process as described in the commonly-assigned U.S. patent application Ser. No. 08/499/353 ("Integrated Process for Handling Saturated and Unsaturated Chlorinated Hydrocarbonaceous Waste and By-Products From Allyl Chloride and Propylene Oxide Processes"), the stream 34 most preferably being finished 1,2-dichloropropane from a chlorohydrin process for making propylene oxide.

Exemplary operating conditions for absorber vessel 32 will be such that the finished 1,2-dichloropropane in stream 34 will be fed to the vessel 32 in a ratio of from about 4 to 5 parts by volume of 1,2-dichloropropane (PDC) per part by volume of the liquid feed portion 30 fed from the vapor-liquid separator 24 to the vessel 32, at a temperature of from about −10 degrees Celsius to about 20 degrees Celsius and at substantially the pressures employed upstream of the absorber vessel 32.

Effluent stream 38 from the absorber vessel 32, containing preferably not more than about 325 parts per million of unsaturated compounds (corresponding approximately to an unsaturated materials content in the liquid feed portion 30 of 1,000 parts per million by weight, and about 150 parts per million of undesirable, unsaturated materials in the finished 1,2-dichloropropane material at a dilution ratio of greater than about 4 parts of 1,2-dichloropropane to 1 part of the liquid feed portion 30), is fed then to a single pass, plug flow-type polishing reactor 40 for essentially completely saturating the unsaturated materials in effluent stream 38 prior to passing the same (directly or indirectly) to a downstream hydrodechlorination portion of an integrated recycle process. As stream 38 from absorber 32 is saturated with hydrogen (corresponding to about 50 parts per million by weight, or 2700 parts per million on a molar basis of hydrogen under typical conditions, for a hydrogen to olefin molar ratio in stream 38 of about 9:1 or greater (i.e., 2700:325 or greater)), it is anticipated that no supplemental hydrogen will need to be added to the reactor 40 for achieving the desired saturation of the effluent stream 38.

By "essentially completely saturating" the unsaturated materials remaining in stream 38 from feed stream 12, it is intended that the polishing reactor product stream 42 contain not more than about 100 parts per million of unsaturated materials, preferably not more than about 50 parts per million of unsaturated materials, more preferably not more than about 20 parts per million of such materials and most preferably not more than about 10 parts per million of unsaturated materials total.

As a qualification to quantifying what constitutes acceptable, preferred and most preferred unsaturated materials levels in product stream 20 and polishing reactor product stream 42 herein, however, it should be noted that depending on the sensitivity of the downstream hydrodechlorination portion and catalyst to various unsaturated materials in the feed stream 12, and depending also on whether unsaturated materials having an undesired effect in the hydrodechlorination portion of an integrated process for handling saturated and unsaturated chlorinated hydrocarbons may be removed from the process in some manner, it may not be necessary to completely saturate all unsaturated materials in the feed stream 12 (and in the stream 34). Rather, what is fundamentally intended is that unsaturated materials which have a negative effect on the hydrodechlorination portion of an integrated process and which are not appropriately or easily removed from the process by some other means be reduced to levels in the polishing reactor product stream 42 which are acceptable in the context of an overall process, by means of the process and apparatus described herein. The figures cited in the preceding paragraph are given as representative of the levels of unsaturated residual chlorinated hydrocarbons from an allyl chloride process which are presently believed to be acceptable and which are preferred in the context of an integrated recycle process as disclosed in commonly-assigned, copending U.S. patent application Ser. No. 08/499,695 (filed concurrently herewith, for "Integrated Process for Handling Saturated and Unsaturated Chlorinated Hydrocarbonaceous Waste and By-Products From Allyl Chloride and Propylene Oxide Processes"), utilizing a catalyst of a type described in commonly-assigned U.S. patent application Ser. No. 08/112, 042, now abandoned, (supported Group VIII/Group Ib alloy catalysts, e.g., platinum/copper alloy catalysts on carbon) or as described more generally (in terms of an active hydrogenating metal component/surface segregating metal component on a support) in commonly-assigned U.S. patent application Ser. No. 08/227,812, filed as a continuation-in-part of the '042 application and now issued as U.S. Pat. No. 5,453,557.

Single pass, plug flow-type polishing reactor 40 can utilize the same or a different saturation catalyst as employed in the primary saturation reactor 14, but it is expected that the same catalyst will preferably be employed and will have a significant lifetime before the catalyst will need to be replaced.

The polishing reactor product stream 42 is then optionally passed to a second, low pressure vapor-liquid separator 44, wherein the stream 42 is degassed and primarily residual hydrogen and hydrogen chloride are separated overhead in a vent stream 46, and a liquid, saturated chlorinated hydrocarbon stream 48 which is substantially free of deleterious and undesired unsaturated materials is produced for further processing in the hydrodechlorination portion of an integrated process such as described for example in commonly-assigned and copending U.S. patent application Ser. No. 08/344,258, in U.S. Pat. No. 4,899,001 to Kalnes et al., U.S. Pat. No. 4,895,995 to James, Jr. et al. or U.S. Pat. No. 4,929,781 to James, Jr. et al.

What is claimed is:

1. A saturation process for essentially completely saturating undesired unsaturated halogenated hydrocarbonaceous materials in a feedstock containing such unsaturated materials, comprising:

accomplishing an initial reduction in the unsaturated halogenated hydrocarbonaceous materials content of the feedstock through contact with hydrogen and a saturation catalyst under saturation conditions in a first reactor;

at least partially condensing the effluent from the first reactor and separating out, in a high pressure vapor-liquid separator, a liquid portion for being recycled in part to the first reactor and a vapor portion for being passed with the remainder of the liquid portion to an absorber vessel;

contacting the vapor portion and liquid portion fed to the absorber vessel with a halogenated . hydrocarbon solvent at substantially the pressures employed in the first saturation reactor and high pressure vapor-liquid separator, whereby unreacted hydrogen and other non-condensable gases in the vapor portion are separated overhead; and passing the bottoms stream from the absorber vessel to a second reactor which is a single pass, plug flow reactor and completing the required saturation of unsaturated halogenated hydrocarbonaceous materials in the feedstock therein through contact with the same or a different saturation catalyst under saturation conditions, whereby the undesired unsaturated halogenated hydrocarbonaceous materials initially found in said feedstock have over the first reactor and the second reactor been essentially completely saturated.

2. A process as defined in claim 1, further comprising degassing the effluent from the second reactor in a low-pressure vapor-liquid separator.

3. A process as defined in claim 1, wherein the feedstock is comprised of dichloropropenes from an allyl chloride process, diluted as necessary with finished 1,2-dichloropropane from a chlorohydrin-based propylene oxide manufacturing process to achieve a total level of unsaturated chlorinated hydrocarbonaceous materials in the feedstock of no more than about 3 percent by weight.

4. A process as defined in claim 3, wherein the feedstock further comprises monochloropropenes in the fractionation overheads of an allyl chloride process.

5. A process as defined in claim 3, wherein the liquid portion fed to the absorber from the high pressure vapor liquid separator contains not more than about 1000 parts per million by weight, total, of the undesired unsaturated chlorinated hydrocarbonaceous materials.

6. A process as defined in claim 5, wherein the solvent employed in the absorber is additional finished 1,2-dichloropropane, and wherein the finished 1,2-dichloropropane solvent is supplied to the absorber in a sufficient amount whereby the bottoms stream from the absorber contains about 325 parts per million or less of the undesired unsaturated chlorinated hydrocarbonaceous materials.

7. A process as defined in claim 6, wherein the effluent from the second reactor contains less than about 100 parts per million or less of the unsaturated chlorinated hydrocarbonaceous materials.

8. A process as defined in claim 7, wherein the effluent from the second reactor contains less than about 50 parts per million or less of the unsaturated chlorinated hydrocarbonaceous materials.

9. A process as defined in claim 8, wherein the effluent from the second reactor contains less than about 20 parts per million or less of the unsaturated chlorinated hydrocarbonaceous materials.

10. A process as defined in claim 9, wherein the effluent from the second reactor contains less than about 10 parts per million or less of the unsaturated chlorinated hydrocarbonaceous materials.

11. A process as defined in claim 4, wherein the liquid portion fed to the absorber from the high pressure vapor liquid separator contains not more than about 1000 parts per million by weight, total, of the undesired unsaturated chlorinated hydrocarbonaceous materials.

12. A process as defined in claim 11, wherein the solvent employed in the absorber is additional finished 1,2-dichloropropane, and wherein the finished 1,2-dichloropropane solvent is supplied to the absorber in a sufficient amount whereby the bottoms stream from the absorber contains about 325 parts per million or less of the undesired unsaturated chlorinated hydrocarbonaceous materials.

13. A process as defined in claim 12, wherein the effluent from the second reactor contains less than about 100 parts per million or less of the unsaturated chlorinated hydrocarbonaceous materials.

14. A process as defined in claim 13, wherein the effluent from the second reactor contains less than about 50 parts per million or less of the unsaturated chlorinated hydrocarbonaceous materials.

15. A process as defined in claim 14, wherein the effluent from the second reactor contains less than about 20 parts per million or less of the unsaturated chlorinated hydrocarbonaceous materials.

16. A process as defined in claim 15, wherein the effluent from the second reactor contains less than about 10 parts per million or less of the unsaturated chlorinated hydrocarbonaceous materials.

17. A saturation process for essentially completely saturating undesired unsaturated halogenated hydrocarbonaceous materials in a feedstock containing such unsaturated materials, comprising:

accomplishing an initial reduction in the unsaturated halogenated hydrocarbonaceous materials content of the feedstock through contact with hydrogen and a saturation catalyst under saturation conditions in a first reactor;

at least partially condensing the effluent from the first reactor and separating out a liquid portion for being recycled in part to the first reactor and a vapor portion for being passed with the remainder of the liquid portion to an absorber vessel;

contacting the vapor portion and liquid portion fed to the absorber vessel with a halogenated hydrocarbon solvent to separate unreacted hydrogen and other non-condensable gases overhead in a vapor stream from the absorber and to provide a liquid bottoms stream;

passing the bottoms stream from the absorber vessel to a single pass second reactor and completing the required saturation of unsaturated halogenated hydrocarbonaceous materials in the feedstock therein through contact with the same or a different saturation catalyst under saturation conditions.

18. A process as defined in claim 17, wherein said reaction in the first reactor, separation of the first reactor effluent, and solvent contact in the absorber are all conducted at substantially the same pressure.

* * * * *